United States Patent [19]
Chalfie et al.

[11] Patent Number: 5,491,084
[45] Date of Patent: Feb. 13, 1996

[54] USES OF GREEN-FLUORESCENT PROTEIN

[75] Inventors: Martin Chalfie, New York, N.Y.; Douglas Prasher, East Falmouth, Mass.

[73] Assignees: The Trustees of Columbia University in the City of New York, New York, N.Y.; Woods Hole Oceanographic Institution, Woods Hole, Mass.

[21] Appl. No.: 119,678

[22] Filed: Sep. 10, 1993

[51] Int. Cl.$^6$ .............................. C12N 9/02; C12N 5/00; C12P 21/06; C07H 19/00

[52] U.S. Cl. .............. 435/189; 435/69.1; 435/69.7; 435/240.2; 435/252.3; 435/320.1; 536/22.1; 536/23.1; 536/23.4; 536/23.5

[58] Field of Search ................................ 435/69.1, 69.7, 435/189, 240.2, 252.3, 320.1; 536/22.1, 23.1, 23.4, 23.5

[56] References Cited

PUBLICATIONS

Gould, S. J., and subrami, S., *Anal. Biochem.*, 175:5 (1988) (Exhibit D).
Silhavy, T. J., and Beckwith, J. R., *Microbiol. Rev.*, 49:398 (1985) (Exhibit E).
Stewart, G. S. A. B., and Williams, P., *J. Gen. Microbiol.*, 138:1289 (1992) (Exhibit F).
Prasher et al. "Primary structure of the *Dequorea victoria* . . ." Gene 111 pp. 229–233 1992.
Glover "Expression of cloned genes in animal cells" *Gene cloning* pp. 179–213 1984.

*Primary Examiner*—Robert A. Wax
*Assistant Examiner*—Hyosuk Kim
*Attorney, Agent, or Firm*—John P. White

[57] ABSTRACT

This invention provides a cell comprising a DNA molecule having a regulatory element from a gene, other than a gene encoding a green-fluorescent protein operatively linked to a DNA sequence encoding the green-fluorescent protein. This invention also provides a method for selecting cells expressing a protein of interest which comprises: a. introducing into the cells a DNAI molecule having DNA sequence encoding the protein of interest and DNAII molecule having DNA sequence encoding a green-fluorescent protein; b. culturing the introduced cells in conditions permitting expression of the green-fluorescent protein and the protein of interest; and c. selecting the cultured cells which express green-fluorescent protein, thereby selecting cells expressing the protein of interest. Finally, this invention provides various uses of a green-fluorescent protein.

12 Claims, 3 Drawing Sheets

5,491,084

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (v i) ORIGINAL SOURCE:
(A) ORGANISM: Escherichia coli (x i) SEQUENCE DESCRIPTION: SEQ ID NO:1:

ACAAAGGCTA GCAAAGGAGA AGAAC  25

USES OF GREEN-FLUORESCENT PROTEIN

The invention disclosed herein was made with Government support under NIH Grant No. 5R01GM30997 from the Department of Health and Human Services. Accordingly, the U.S. Government has certain rights in this invention.

BACKGROUND OF THE INVENTION

Throughout this application various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

Several methods are available to monitor gene activity and protein distribution within cells. These include the formation of fusion proteins with coding sequences for β-galactosidase (21), and luciferases (21). The usefulness of these methods is often limited by the requirement to fix cell preparations or to add exogenous substrates or cofactors. This invention disclose a method of examining gene expression and protein localization in living cells that requires no exogenously-added compounds.

This method uses a cDNA encoding the Green-Fluorescent Protein (GFP) from the jelly fish *Aequorea victoria* (5). In A. victoria, GFP absorbs light generated by aequorin upon the addition of calcium and emits a green light.

This invention discloses that GFP expressed in prokaryotic and eukaryotic cells is capable of producing a strong green fluorescence when excited near UV or blue light. Since this fluorescence requires no additional gene products from *A. victoria*, chromophore formation is not species specific.

SUMMARY OF THE INVENTION

This invention provides a cell comprising a DNA molecule having a regulatory element from a gene, other than a gene encoding a green-fluorescent protein operatively linked to a DNA sequence encoding the green-fluorescent protein.

This invention provides a method for selecting cells expressing a protein of interest which comprises: a) introducing into the cells a DNAI molecule having DNA sequence encoding the protein of interest and DNAII molecule having DNA sequence encoding a green-fluorescent protein; b) culturing the introduced cells in conditions permitting expression of the green-fluorescent protein and the protein of interest; and c) selecting the cultured cells which express green-fluorescent protein, thereby selecting cells expressing the protein of interest.

This invention also provides a method for localizing a protein of interest in a cell: a. introducing into a cell a DNA molecule having DNA sequence encoding the protein of interest linked to DNA sequence encoding a green-fluorescent protein such that the protein produced by the DNA molecule will have the protein of interest fused to the green-fluorescent protein; b. culturing the cell in conditions permitting expression of the fused protein; c. detecting the location of the green-fluorescent protein in the cell, thereby localizing a protein of interest in a cell.

DETAILED DESCRIPTION OF THE INVENTION

Figure 1:
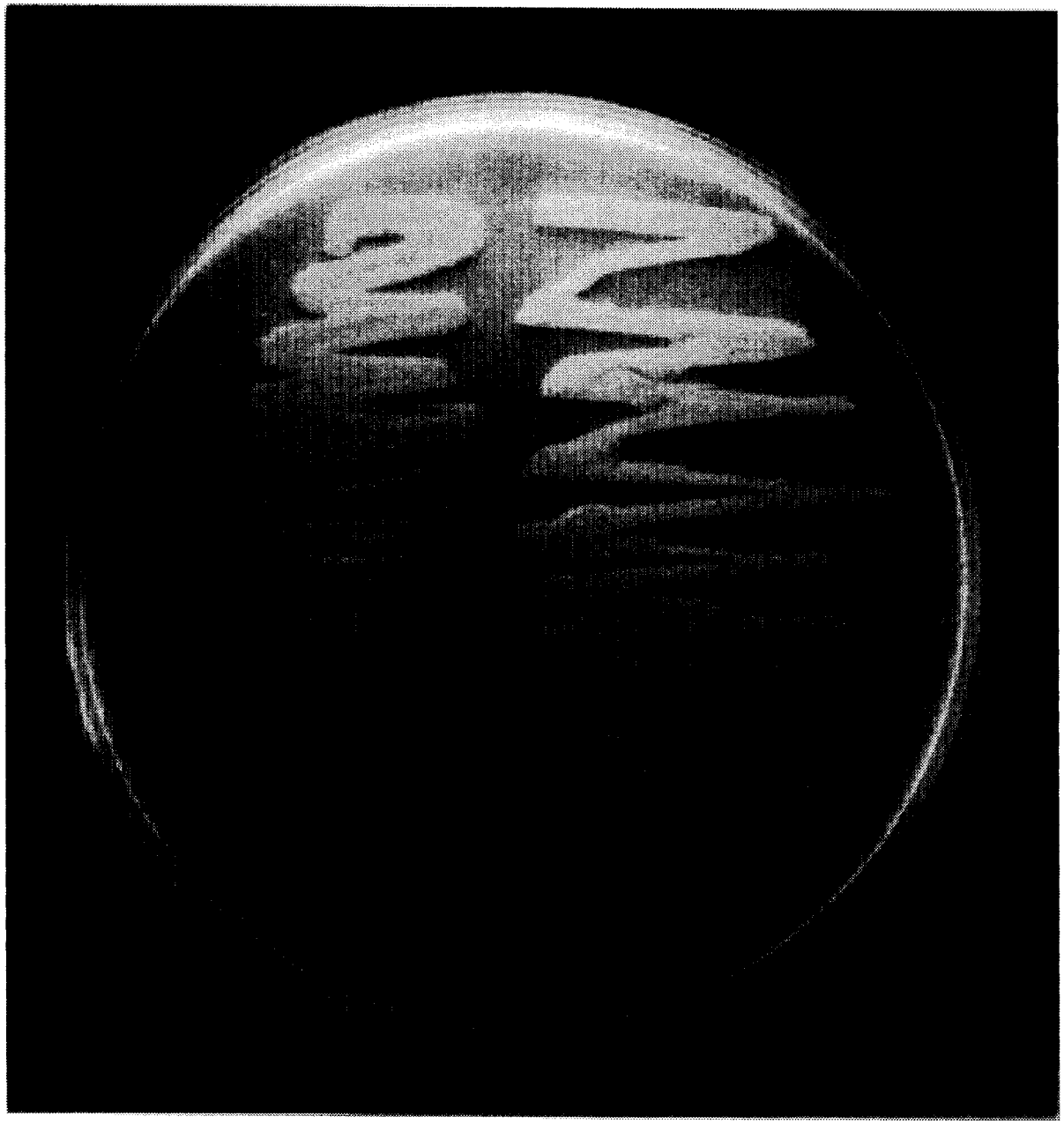
FIG. 1 Expression of GFP in *E. coli*. The bacteria on the right side of the figure have the GFP expression plasmid. This photograph was taken while irradiating the plate with a hand-held long-wave UV source.

Throughout this application, the following standard abbreviations are used to indicate specific nucleotides:

| C = cytosine | A = adenosine |
|---|---|
| T = thymidine | G = guanosine |

This invention provides a cell comprising a DNA molecule having a regulatory element from a gene, other than a gene encoding a green-fluorescent protein operatively linked to a DNA sequence encoding the green-fluorescent protein.

This invention provides a cell comprising a DNA molecule having a regulatory element from a gene, other than a gene encoding a green-fluorescent protein operatively linked to a DNA sequence encoding the green-fluorescent protein, wherein the cell is selected from a group consisting essentially of bacterial cell, yeast cell, fungal cell, insect cell, nematode cell, plant or animal cell.

Suitable animal cells include, but are not limited to Vero cells, HeLa cells, Cos cells, CV1 cells and various primary mammalian cells.

In an embodiment, the bacterial cell is *Escherichia coli*.

As used herein, "a regulatory element" from a gene is the DNA sequence which is necessary for the expression of the gene.

In this invention, the term "operatively linked" to means that following such a link the regulatory element can direct the expression of the linked DNA sequence which encodes a green-fluorescent protein.

The gene encoding a green-fluorescent protein includes DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms.

These DNA molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

As an example, plasmid pGFP10.1 codes for a mutated GFP protein with the 80th codon changed from a glutamine to arginine. This mutated protein retains the property of the natural protein.

In an embodiment, the regulatory element is a promoter. In a further embodiment, the promoter is activated by a heavy metal. Such promoters are well-known in the art (J. H.

Freedman, L. W. Slice, A. Fire, and C. S. Rubin (1993) *Journal of Biological Chemistry*, 268:2554).

In another embodiment, the promoter is a P450 promoter. Cytochrome P450 is well-known in the art and there are a number of P450 promoters known.

In still another embodiment, the promoter is for a stress protein. Such stress proteins are well-known in the art (E. G. Stringham, D. K. Dixon, D. Jones and E. D. Candido (1992) *Molecular Biology of the Cell*, 3:221; and William J. Welch (May, 1993), *Scientific American*, page 56). In a further embodiment, the stress protein is a heat-shock protein.

This invention provides a cell comprising a DNA molecule having a regulatory element from a gene, other than a gene encoding a green-fluorescent protein operatively linked to a DNA sequence encoding the green-fluorescent protein, wherein the promoter is for a gene viable to the cell growth.

In another embodiment, the regulatory element is an enhancer. Enhancers are well-known in the art.

This invention provides a cell comprising a DNA molecule having a regulatory element from a gene, other than a gene encoding a green-fluorescent protein operatively linked to a DNA sequence encoding the green-fluorescent protein, wherein the DNA sequence encoding the *Aequorea victoria* green-fluorescent protein.

In an embodiment, the *Aequorea victoria* green-fluorescent protein is cloned in a plasmid. This plasmid is a modification of the pBS(+) (formerly called pBluescribe +) vector (Stratagene®) which has inserted within it an Eco RI fragment containing the cDNA sequence of the *Aequorea victoria* green-fluorescent protein (as modified herein). The fragment was obtained from λGFP10 (Prasher, D. C., Eckenrode, V. K., Ward, W. W., Prendergast, F. G., and Cormier, M. J., (1992) Primary structure of the *Aequorea victoria* green-fluorescent protein. *Gene*, 111:229–233) by amplification using the polymerase chain reaction (Saiki, R. K., Gelfand, D. H., Stoffel, S., Sharf, S. J., Higuchi, G. T., Horn, G. T., Mullis, K. B., and Erlich, H. A. (1988) Primer-directed enzymatic amplification of DNA with a thermostable DNA polymerase. *Science*, 239:487–491) with primers flanking the Eco RI sites and subsequent digestion with Eco RI. The sequence of the cDNA in pGFP10.1 differs from the published sequence (5) by a change of the 80th codon of the coding sequence from CAG to CGG, a change that produces a glutamine to arginine change in the protein sequence.

This pGFP10.1 plasmid was deposited on Sep. 1, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid pGFP10.1 was accorded ATCC Accession Number 75547.

This invention provides a living organism comprising the cell comprising a DNA molecule having a regulatory element from a gene, other than a gene encoding a green-fluorescent protein operatively linked to a DNA sequence encoding the green-fluorescent protein.

In an embodiment, the living organism is *C. elegans*. In another embodiment, the living organism is Drosophila, zebra fish or bacteriophage.

A bacteriophage carrying the green-fluorescent protein gene can infect a particular type of bacteria. The infection may be easily detected via the expression of the green-fluorescent protein. Therefore, by using appropriate bacteriophages, the presence of that particular type of bacteria may be detected.

Similarly, a virus carrying the green-fluorescent protein gene may infect a specific cell type. The infection may be easily detected by monitoring the expression of the green-fluorescent protein.

The above-described cells and living organisms are useful to detect effects of external stimulus to the regulatory element. The stimulus may have direct or indirect effects on the regulatory element. Such effects will be detectable through either the induction of expression and production of the green-fluorescent protein or switching off the expression of the green-fluorescent protein.

Cells expressing the green-fluorescent proteins may be conveniently separated by a fluorescence-activated cell sorter.

These cells and organisms may be used to detect the presence of different molecules in various kinds of biological samples such as blood, urine or saliva. By operatively linking a regulatory element of the gene which is affected by the molecule of interest to a green-fluorescent protein, the presence of the molecules will affect the regulatory element which in turn will affect the expression of the green-fluorescent protein. Therefore, the above-described cells are useful for the detection of molecules. Such detection may be used for diagnostic purposes. An example of such a molecule is a hormone.

This invention provides a living organism comprising the cell comprising a DNA molecule having a regulatory element from a gene, other than a gene encoding a green-fluorescent protein operatively linked to a DNA sequence encoding the green-fluorescent protein, wherein the regulatory element is for a stress protein.

This invention provides a living organism comprising the cell comprising a DNA molecule having a regulatory element from a gene, other than a gene encoding a green-fluorescent protein operatively linked to a DNA sequence encoding the green-fluorescent protein, wherein the stress protein is a heat-shock protein.

This invention provides a method for selecting cells expressing a protein of interest which comprises: a) introducing into the cells a DNAI molecule having DNA sequence encoding the protein of interest and DNAII molecule having DNA sequence encoding a green-fluorescent protein; b) culturing the introduced cells in conditions permitting expression of the green-fluorescent protein and the protein of interest; and c) selecting the cultured cells which express green-fluorescent protein, thereby selecting cells expressing the protein of interest.

This invention also provides the above method, wherein the cells are selected from a group consisting essentially of bacterial cells, yeast cells, fungal cells, insect cells, nematode cells, plant or animal cells. Suitable animal cells include, but are not limited to Vero cells, HeLa cells, Cos cells, CV1 cells and various primary mammalian cells.

In an embodiment, DNAI and DNAII are linked. In another embodiment, the DNA encodes the *Aequorea victoria* green-fluorescent protein.

This invention provides a method for localizing a protein of interest in a cell which comprises: a) introducing into a cell a DNA molecule having DNA sequence encoding the protein of interest linked to DNA sequence encoding a green-fluorescent protein such that the protein produced by the DNA molecule will have the protein of interest fused to the green-fluorescent protein; b) culturing the cell in conditions permitting expression of the fused protein; and c) detecting the location of the green-fluorescent protein in the cell, thereby localizing a protein of interest in a cell.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general.

The host cell of the above expression system may be selected from the group consisting of the cells where the protein of interest is normally expressed, or foreign cells such as bacterial cells (such as *E. coli*), yeast cells, fungal cells, insect cells, nematode cells, plant or animal cells, where the protein of interest is not normally expressed. Suitable animal cells include, but are not limited to Veto cells, HeLa cells, Cos cells, CV1 cells and various primary mammalian cells.

In an embodiment of the method for localizing a protein of interest in a cell, the DNA encoding the green-fluorescent protein is from *Aequorea victoria*.

This invention provides a method for localizing a protein of interest in a cell which comprises: a) introducing into a cell a DNA molecule having DNA sequence encoding the protein of interest linked to DNA sequence encoding a green-fluorescent protein such that the protein produced by the DNA molecule will have the protein of interest fused to the green-fluorescent protein; b) culturing the cell in conditions permitting expression of the fused protein; and c) detecting the location of the green-fluorescent protein in the cell, thereby localizing a protein of interest in a cell, wherein the cell normally expressing the protein of interest.

This invention provides a method for detecting expression of a gene in a cell which comprises: a) introducing into the cell a DNA molecule having DNA sequence of the gene linked to DNA sequence encoding a green-fluorescent protein such that the regulatory element of the gene will control expression of the green-fluorescent protein; b) culturing the cell in conditions permitting expression of the gene; and c) detecting the expression of the green-fluorescent protein in the cell, thereby indicating the expression of the green in the cell.

This invention provides a method for indicating expression of a gene in a subject which comprises: a) introducing into a cell of the subject a DNA molecule having DNA sequence of the gene linked to DNA sequence encoding a green-fluorescent protein such that the regulatory element of the gene will control expression of the green-fluorescent protein; b) culturing the cell in conditions permitting expression of the fused protein; and c) detecting the expression of the green-fluorescent protein in the cell, thereby indicating the expression of the gene in the cell.

In an embodiment of the above methods, the green-fluorescent protein is the *Aequorea victoria* green-fluorescent protein.

This invention provides a method for determining the tissue-specificity of a DNA sequence in a subject which comprises: a) introducing into a cell of the subject a DNA molecule having the DNA sequence linked to DNA sequence encoding a green-fluorescent protein such that the DNA sequence will control expression of the green-fluorescent protein; b) culturing the subject in conditions permitting the expression of the green-fluorescent protein; and c) detecting the expression of the green-fluorescent protein in different tissue of the subject, thereby determining the tissue-specificity of the DNA sequence.

This invention provides a method for determining the presence of heavy metal in a solution which comprises: a) culturing the cell comprising a DNA molecule having a promoter from a gene, other than a green-fluorescent protein operatively linked to a DNA sequence encoding the green-fluorescent protein, wherein the promoter is activated by a heavy metal in the solution; and b) detecting expression of the green-fluorescent protein, the expression of the green-fluorescent protein indicates the presence of heavy metal.

This invention provides a method for detecting pollutants in a solution which comprises: a) culturing the cell comprising a DNA molecule having a promoter from a gene, other than a green-fluorescent protein operatively linked to a DNA sequence encoding the green-fluorescent protein, wherein the promoter is activated by a heavy metal or the promoter is for a stress protein in the solution; and b) detecting expression of the green-fluorescent protein, the expression of the green-fluorescent protein indicates the presence of heavy metal.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Light is produced by the bioluminescent jellyfish *Aequorea victoria* when calcium binds to the photoprotein aequorin (1). Although activation of aequorin in vitro or in heterologous cells produces blue light, the jellyfish produces green light. This latter light is due to the presence of a second protein in *A. victoria* called the green-fluorescent protein (GFP) that absorbs the energy from aequorin (2).

Purified GFP absorbs blue light (maximally at 395 nm with a minor peak at 470 m) and emits green light (peak emission at 509 nm with a shoulder at 540 nm) (2, 3). This fluorescence is very stable; virtually no photobleaching is observed (4). As recently deduced from a cDNA clone from *A. victoria*, GFP is a protein of 238 amino acids (5). Although the intact protein is needed for fluorescence, the same absorption spectral properties as the denatured protein are found in a hexapeptide starting at amino acid 64 (6, 7). The GFP chromophore is derived from the primary amino acid sequence through the cyclization of Ser-dehydroTyr-Gly within this hexapeptide (7). The mechanisms that produce the dehydrotyrosine and cyclize the polypeptide to form the chromophore are unknown. To determine whether additional factors from *A. victoria* were needed for the production of the fluorescent protein, applicants tested GFP fluorescence in heterologous systems. Applicants show here that GFP expressed in prokaryotic and eukaryotic cells is capable of producing a strong green fluorescence when excited by blue light. Since this fluorescence requires no additional gene products from *A. victoria*, chromophore formation is not species specific and occurs either through the uses of ubiquitous cellular components or by autocatalysis.

Figure 2:
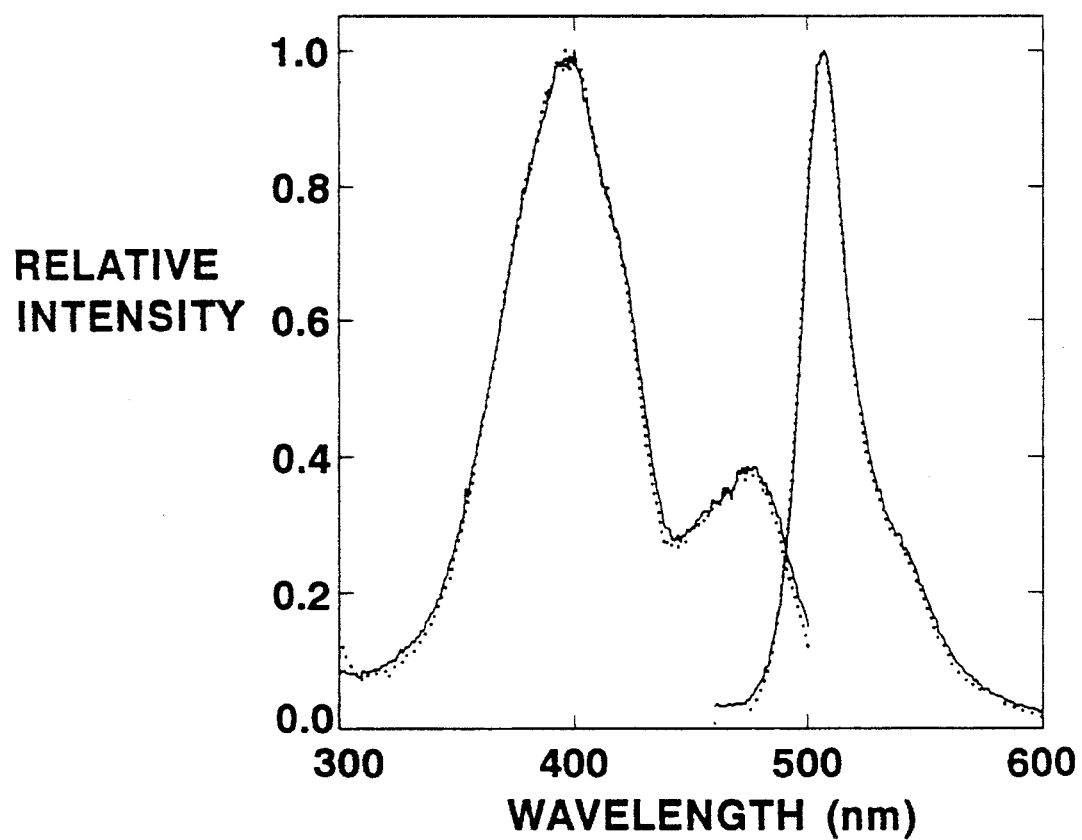
FIG. 2 Excitation and Emission Spectra of *E. coli*-generated GFP (solid lines) and purified *A. victoria* GFP (L form; dotted lines).

Expression of GFP in *Escherichia coli* (8) results in an easily detected green fluorescence (9) that is not seen in control bacteria. For example, florescent bacteria were easily seen on plates containing IPTG when they were illuminated with a long-wave UV source (FIG. 1). Since the cells grow well in the continual presence of the inducer (IPTG), GFP does not appear to have a toxic effect on the cells. When GFP was partially purified from this strain (10), it was found to have fluorescence excitation and emission spectra indistinguishable form those of the purified native protein (FIG. 2). The spectral properties of the recombinant GFP suggest that the chromophore can form in the absence of other *A. victoria* products.

Figure 3:
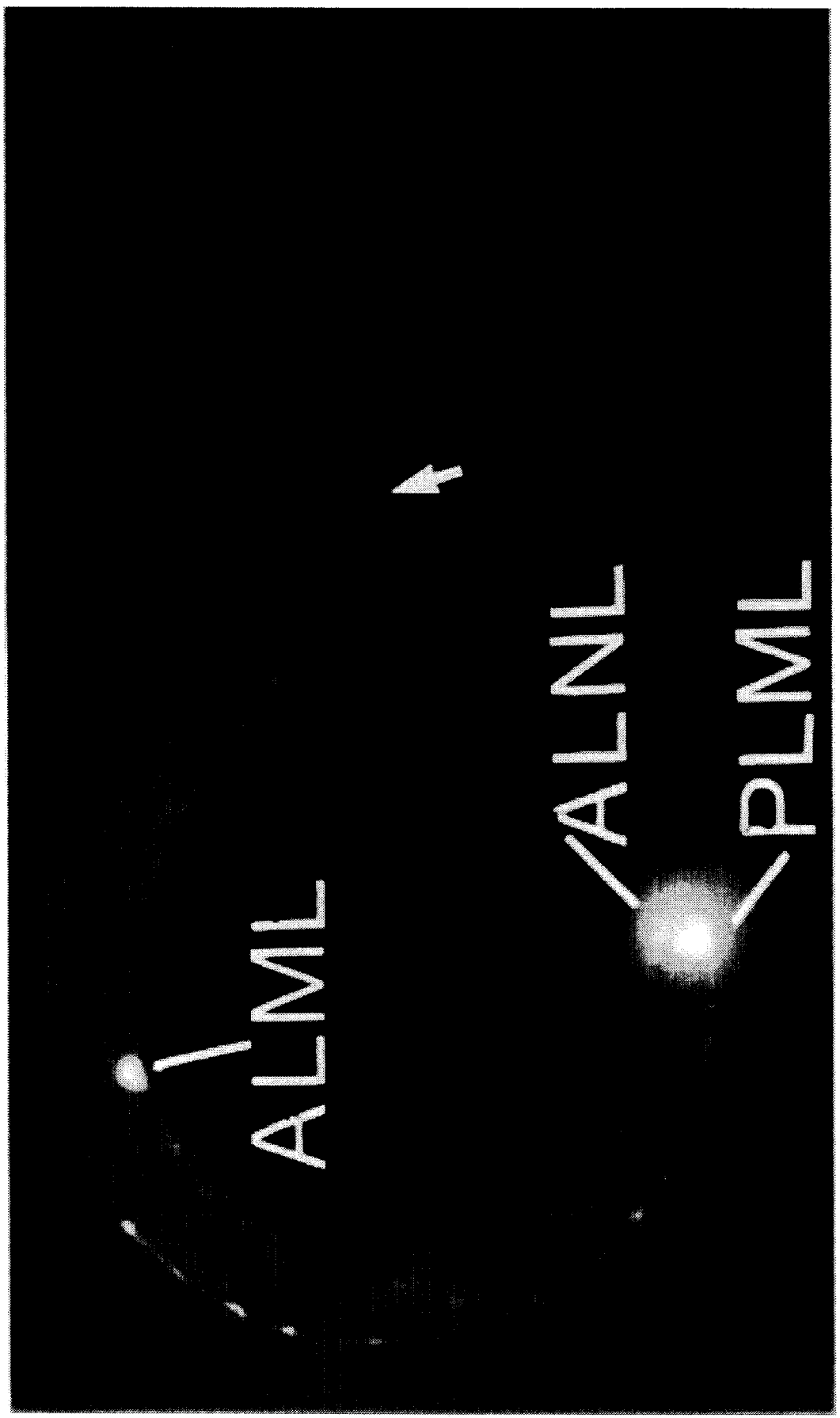
FIG. 3 Expression of GFP in a first stage Caenorhabditis elegans larva. Two touch receptor neurons (PLML and ALML) and one other neuron of unknown function (ALNL) are indicated. Processes can be seen projecting from all three cell bodies. The arrow points to the nerve ring branch from the ALML cell (out of focus). The background fluorescence is due to the animal's autofluorescence.

Transformation of the nematode *Caenorhabditis elegans* also resulted in the production of fluorescent GFP (11) (FIG. 3). GFP expression was directed to a relatively small number of neurons using a promoter for the mec-7 gene. This gene encodes a β-tubulin (12) that is expressed strongly in six touch receptor neurons in *C. elegans* and weakly in a few other neurons (13, 14). The pattern of expression of GFP was similar to that seen with the anti-MEC-7 antibody or from mec-7lacZ fusions (13–15). The strongest fluorescence was seen in the cell bodies of the four embryonically-derived touch receptor neurons (ALML, ALMR, PLML, PLMR). The processes from these cells, including their terminal branches, were often easily seen in larval animals. In older larvae, the cell bodies of the remaining touch cells (AVM and PVM) were also seen; the processes of these cells were more difficult to detect. These postembryonically-derived cells arise during the first of the four larval stages (16), but their outgrowth occurs in the following larval stages (17) with the cells becoming functional during the fourth larval stage (18). GFP's fluorescence in these cells is consistent with these previous results; no newly hatched or late first-stage larvae, and seven of eight young adults had at least one of these cells (19). In addition, moderate to weak fluorescence was seen for a few other neurons (FIGS. 3, and 20).

The expression of GFP in both *E. coli* and *C. elegans* differs from that of the native protein in one respect. Although relatively stable when illuminated using low intensities of 470 nm light, the fluorescence photobleaches rapidly (within seconds) when the cells are illuminated with light of approximately 395 nm. Applicants do not know whether this difference is caused by the alteration of the protein-coding sequence (8), by the absence of a necessary post-translational modification, or by non-specific damage within the cells. However, when cells in *C. elegans* have been photobleached, some recovery is seen within 10 minutes. Further investigation is needed to determine whether this recovery represents de novo synthesis of GFP.

Several methods are available to monitor gene activity and protein distribution within cells. These include the formation of fusion proteins with coding sequences for β-galactosidase, firefly luciferase, and bacterial luciferase (21). Because these methods require exogenously-added substrates or cofactors, they are of limited use with living tissue. Since detection of intracellular GFP requires only the radiation by near UV or blue light, it is not substrate limited. Thus, it should provide an excellent means of monitoring gene expression and protein localization in living cells (22).

Because it does not appear to interfere with cell growth and function, GFP should also be a convenient indicator of transformation (and one that could allow cells to be separated using fluorescence-activated cell sorting). Applicants also envision that GFP can be used as a vital marker so that cell growth (for example, the elaboration of neuronal processes) and movement can be followed in situ, especially in animals that are essentially transparent like *C. elegans* and zebra fish.

References and notes

1. Shimomura, O., Johnson, F. H., Saiga, Y., (1962) *J. Cell. Comp. Physiol.*, 59:223.

2. Morise, H., Shimomura, O., Johnson, F. H. and Winant, J. (1974), *Biochemistry*, 13:2656.

3. Ward, W. W., Cody, C. W., Hart, R. C. and Cormier, M. J., (1980), *Photochem. Photobiol.*, 31:611.

4. Prendergast, F. G., personal communication.

5. Prasher, D. C., Eckenrode, V. K., Ward, W. W., Prendergast, F. G., and Cormier, M. J., (1992), *Gene*, 111:229.

6. Shimomura, A., (1979), *FEBS Lett.*, 104:220.

7. Cody, C. W., Prasher, D. C., Westler, W. M., Prendergast, F. G., and Ward, W. W., (1993), *Biochemistry*, 32:1212.

8. Plasmid pGFP10.1 was formed by placing the Eco RI fragment encoding the GFP cDNA from λgfp10 (5) into pBS(+) (Stratagene®). The fragment was obtained by amplification using the polymerase chain reaction (PCR; R. K. Saiki, et al., *Science*, 239:487 (1988)) with primers flanking the Eco RI sites and subsequent digestion with Eco RI. The sequence of the cDNA in pGFP10.1 differs from the published sequence by a change in codon 80 within the coding sequence from CAG to CGG, a change that replaces a glutamine residue with arginine. As seen in FIG. 2, this replacement has no detectable effect on the spectral properties of the protein.

An *E. coli* expression construct was made by using PCR to generate a fragment with an Nbe I site at the start of translation and an Eco RI site 5' primer was ACAAAG-GCTAGCAAAGGAGAAGAAC (Sequence ID No.: 1) and the 3' primer was the T3 primer (Stratagene®). The Nhe I-Eco RI fragment was ligated into the similarly cut vector pET3a [A. H. Rosenberg., et al., *Gene*, 56:125, (1987)] by standard methods [J. Sambrook, E. F., Fritsch, and T. Maniatis, *Molecular cloning: A laboratory manual*, 2nd ed., Cold Spring Harbor Laboratory Press, Cold Spring Harbor, N.Y., (1989)]. The *E. coli* strain BL21(DE3)Lys [F. W. Studier and B. A. Moffat, *J. Mol. Biol.*, 189:113 (1986)] was transformed with the resulting plasmid (TU#58) and grown at 37°. Control bacteria were transformed with pET3a. Animals were grown on nutrient plates containing 100 μg/ml ampicillin and 0.8 mM IPTG.

9. A variety of microscopes have been used for these experiments with epifluorescence filter sets normally used for fluorescein isothiocyanate. In addition, as might be expected from its spectral characteristics a Xenon lamp gave a more intense fluorescence than a mercury lamp when cells were illuminated with light round 470 nm. No other attempts were made to enhance the signal (for example, by using low intensity light cameras), although it is may be useful in some instances.

10. GFP was purified from 250 ml cultures of BL21(DE3)Lys S bacteria containing TU#58; bacteria were grown in LB broth [J. Sambrook, et al., op. cit.] containing 100 μg/ml ampicillin and 0.8 mM IPTG. Applicants fount that induction was best when IPTG was present continually. Cells were washed in 4 ml of 10 mM Tris. HCl pH 7.4, 100 mM NaCl, 1 mM $MgCl_2$, and 10 mM dithiothreitol [A. Kumagai and W. G. Dunphy, *Cell*, 64:903 (1991)] and then sonicated (2×20 sec) in 4 ml of the same buffer containing 0.1 mM PMSF, 1 μg/ml pepstatin A, 1 μg/ml leupeptin, and 2 μg/ml aprotinin, and centrifuge at 5,000 rpm for 5' in the cold. The supernatant was centrifuged a second time (15,000 rpm for 15') and then diluted seven fold with 10 mM Tris pH 8.0, 10 mM EDTA and 0.02% $NAN_3$. Corrected excitation and emission spectra were obtained using a SPEX FIT11 Spectrofluormeter and compared with purified L-form GFP from *A. victoria* (M. Cutler, A. Roth and W. W. Ward, unpublished data). The excitation spectra were measured from 300–500 nm with a fixed emission wavelength of 509 nm and the emission spectra, were measured from 410–600 nm with a fixed excitation of 395 nm. All spectra were recorded as signal/reference data (where the reference is a direct measurement of the lamp intensity using a separate photomultiplier tube) at room temperature with 1 second integration time and 1 nm increment. The spectral hand width were adjusted to 0.94 nm for all spectra.

11. Wild-type and mutant animals were grown and genetic strains were constructed according to S. Brenner, *Genetics*, 77:71 (1974).

The plasmid p3FP10.1 was used as a template in PCR to generate a fragment with a 5' Nhe I site (at the start of translation) and a 3' Eco RI site (3' of the termination codon). The DNA was cut to produce an Nhe I-Eco RI fragment that was ligated into plasmid pPD 16.51 [12; A. Fire, S. W. Harrison, and D. Dixon, *Gene*, 93:189 (1990)], a vector containing the promoter of the *C. elegans* mec-7 gene. Wild-type *C. elegans* were transformed by coinjecting this DNA (TU#64) and the DNA for plasmid pRF4, which contains the dominant rol-6 (su1006) mutation, into adult gonads as described by C. M. Mello, J. M. Kramer, D. Stinchcomb, and V. Ambros, *EMBO J.*, 10:3959 (1991). A relatively stable line was isolated (TU1710) and the DNA it carried was integrated as described by Mitani et al. (15) to produce the integrated elements uIs3 and uIs4 (in strains TU1754 and TU1755, respectively).

Live animals were mounted on agar (or agarose) pads as described by Sulston and Horvitz (16), often with 10 mM NaN$_3$ as an anesthetic (G. Nelson, pers. comm.) and examined using either a Zeiss universal or axiophot microscope. For *C. elegans*, applicants find that a long-pass emission filter works best, because the animal's intestinal autofluorescence, which increases as the animal matures, appears yellow (with band-pass filters the autofluorescence appears green and obscures the GFP fluorescence).

Because much more intense fluorescence was seen in uIs4 than uIs3 animals (for example, it was often difficult to see the processes of the ALM and PLM cells in uIs3 animals using a mercury lamp), the former have been used entirely for the observations reported here. The general pattern of cell body fluorescence was the same in both strains and in the parental, nonintegrated strain (fluorescence in this strain was strong like in the uIs4 animals). The uIs4 animals, however, did show an unusual phenotype; both the ALM and PLM touch cells were often displaced anteriorly. These cells usually showed the correct pattern of outgrowth, although occasional cells had abnormally projecting processes. These cells could be identified as touch receptor cells, since the fluorescence was dependent on mec-3, a homeobox gene that specifies touch cell fate [13, 15, 18, J. C. Way and M. Chalfie, *Cell*, 54:5 (1988)]. It has been shown previously that mec-7 expression is reduced in the ALM touch cells of the head (but not as dramatically in the PLM touch cells of the tail) in mec-3 gene mutants (13, 15). Applicants find a similar change of GfP expression in a mec-3 mutant background for both uIs3 and uIs4. Thus, GFP accurately mimics the known expression pattern of the mec-7 gene. It is likely that the reduced staining in uIs3 animals and the misplaced cells in uIs4 animals is due either to secondary mutations or the amount and position of the integrated DNA.

12. Savage, C., Hamelin, M., Culotti, J. G., Coulson, A., Albertson, D. G., and Chalfie, M., *Genes. Dev.*, 3:870, (1989).

13. Hamelin, M., Scott, I. M., Way, J. C., Culotti, J. G., (1992) *EMBO J.*, 11:2885.

14. Duggan, A., and Chalfie, M., unpublished data.

15. Mitani, S., Du, H. P., Hall, D. H., Driscoll, M., and Chalfie, M., (1993), *Development*, in press.

16. Sulston, J. E., and Horvitz, H. R., (1977), *Develop. Biol.*, 56:110.

17. Walthall, W. W. and Chalfie, M., (1988), *Science*, 239:643.

18. Chalfie, M., and Sulston, J., (1981), *Dev. Biol.*, 82:358.

19. In adults, the thicker size of the animals and the more intense autofluorescence of the intestine tend to obscure these cells.

20. These include several cells in the head (including the FLP cells) and tail of newly hatched animals and the BDU cells, a pair of neurons just posterior to the pharynx. Such cells have been seen previously (13, 15). The strongest staining of these non-touch receptor neurons are a pair of cells in the tail that have anteriorly-directed processes that project along the dorsal muscle line. It is likely that these are the ALN cells, the sister cells to the PLM touch cells [J. G. White, E. Southgate, J. N. Thomson, and S. Brenner, *Philos. Trans. R. Soc. Lond. B. Biol. Sci*, 314:1 (1986)].

21. Reviewed in T. J. Silhavy and J. R. Beckwith, *Microbiol. Rev.* 49:398 (1985); S. J. Gould and S. Subramani, *Anal. Biochem.* 175:5 (1988; and G. S. A. B. Stewart and P. Williams, *J. Gen. Microbiol.*, 138:1289 (1992).

22. Applicants have generated several other plasmid constructions that may be useful to investigators. These include a pBluescript II KS (+) derivative (TU#65) containing a Kpn I-Eco RI fragment encoding GFP with an Age I site 5' to the translation start and a BAM I site at the termination codon. Also available are gfp versions (TU#60–TU#63) of the four *C. elegans* lacZ expression vectors (pPD16.43, pPD21.28, pPD22.04, and pPD22.11, respectively) described by Fire, et al., 1990 (op. cit.).

What is claimed is:

1. A host cell comprising a DNA molecule having a regulatory element from a gene, other than a gene encoding an *Aequorea victoria* green-fluorescent protein operatively linked to a DNA sequence encoding the fluorescent *Aequorea victoria* green-fluorescent protein.

2. A cell of claim 1, wherein the cell is selected from a group consisting of bacterial cell, yeast cell, fungal cell, plant cell or animal cell.

3. A cell of claim 1, wherein the regulatory element is a promoter.

4. A cell of claim 3, wherein the promoter is activated by a heavy metal.

5. A cell of claim 3, wherein the promoter is a P450 promoter.

6. A cell of claim 3, wherein the promoter is from a gene encoding a stress protein.

7. A cell of claim 6, wherein the stress protein is a heat-shock protein.

8. A cell of claim 1, wherein the regulatory element is an enhancer.

9. A method for selecting cells expressing a protein of interest which comprises:

(a) introducing into the cells a DNAI molecule having DNA sequence encoding the protein of interest and DNAII molecule having DNA sequence encoding an *Aequorea victoria* green-fluorescent protein;

(b) culturing the introduced cells in conditions permitting expression of the *Aequorea victoria* green-fluorescent protein and the protein of interest; and (c) selecting the cultured cells which express *Aequorea victoria* green-fluorescent protein, thereby selecting cells expressing the protein of interest, wherein DNAI and DNAII are linked.

10. A method for selecting cells expressing a protein of interest which comprises:

(a) introducing into the cells a DNAI molecule having DNA sequence encoding the protein of interest and DNAII molecule having DNA sequence encoding an *Aequorea victoria* green-fluorescent protein;

(b) culturing the introduced cells in conditions permitting expression of the *Aequorea victoria* green-fluorescent protein and the protein of interest; and (c) selecting the cultured cells which express *Aequorea victoria* green-fluorescent protein, thereby selecting cells expressing the protein of interest, wherein the cells are selected from a group consisting of yeast cells, fungal cells, insect cells, nematode cells, plant or animal cells.

11. A method for localizing a protein of interest in a cell which comprises:

(a) introducing into a cell a DNA molecule having DNA sequence encoding the protein of interest linked to DNA sequence encoding an *Aequorea victoria* green-fluorescent protein such that the protein produced by the DNA molecule will have the protein of interest fused to the *Aequorea victoria* green-fluorescent protein;

(b) culturing the cell in condition permitting expression of the fused protein; and (c) detecting the location of the fluorescence of the fused protein in the cell, thereby localizing a protein of interest in a cell.

12. A method of claim 11, wherein the cell normally expresses the protein of interest.

* * * * *